United States Patent
Chang et al.

(10) Patent No.: US 10,650,557 B2
(45) Date of Patent: May 12, 2020

(54) FOCUS DETECTION APPARATUS AND METHOD THEREOF

(71) Applicant: TAIHAO MEDICAL INC., Taipei (TW)

(72) Inventors: Ruey-Feng Chang, Taichung (TW);
Jen-Feng Hsu, Taoyuan (TW);
Hong-Hao Chen, Hsinchu (TW);
Rong-Tai Chen, Taichung (TW);
Tsung-Chen Chiang, Kaohsiung (TW);
You-Wei Wang, New Taipei (TW);
Hsin-Hung Lai, Taipei (TW)

(73) Assignee: TAIHAO MEDICAL INC., Taipei (TW)

( * ) Notice: Subject to any disclaimer, the term of this patent is extended or adjusted under 35 U.S.C. 154(b) by 89 days.

(21) Appl. No.: 16/170,058

(22) Filed: Oct. 25, 2018

(65) Prior Publication Data
US 2019/0147629 A1    May 16, 2019

(30) Foreign Application Priority Data
Nov. 10, 2017 (TW) ............................... 106139059 A

(51) Int. Cl.
*A61B 6/00* (2006.01)
*G06T 11/00* (2006.01)
(Continued)

(52) U.S. Cl.
CPC ............ *G06T 11/008* (2013.01); *A61B 6/032* (2013.01); *A61B 6/504* (2013.01); *A61B 6/5217* (2013.01);
(Continued)

(58) Field of Classification Search
CPC .................................. A61B 6/00; G06T 11/00
(Continued)

(56) References Cited

U.S. PATENT DOCUMENTS

| 7,466,848 B2 | 12/2008 | Metaxas et al. |
| 9,084,578 B2 * | 7/2015 | Lee ................... A61B 6/502 |

(Continued)

FOREIGN PATENT DOCUMENTS

| CN | 103455821 | 12/2013 |
| CN | 105701331 | 6/2016 |

(Continued)

OTHER PUBLICATIONS

Gallego-Posada; J. D. et al, "Detection and Diagnosis of Breast Tumors using Deep Convolutional Neural Networks," Research Practice on Mathematical Modeling School of Mathematical Sciences, Jun. 2016, pp. 1-9.

(Continued)

*Primary Examiner* — Abolfazl Tabatabai
(74) *Attorney, Agent, or Firm* — JCIPRNET

(57) ABSTRACT

A focus detection apparatus and a method thereof are provided. In the method, a medical image is obtained. Size of a target focus and a sliding window are determined, and side length of the sliding windows is at least twice the side length of the target focus. The medical image is scanned through the sliding window, and a stride which the sliding windows moves each time is not greater than the side length of the target focus. At least one area of interest is obtained based on the scan result. Then, the area of interest is identified based on machine learning techniques, and perform candidate aggregation and multiple size aggregation to determine at least one focus position. Accordingly, the computational time and the detection accuracy can be improved.

10 Claims, 6 Drawing Sheets

(51) Int. Cl.
*A61B 8/08* (2006.01)
*A61B 6/03* (2006.01)
*A61B 5/00* (2006.01)

(52) U.S. Cl.
CPC .......... *A61B 8/5223* (2013.01); *G06T 11/005* (2013.01); *A61B 5/4312* (2013.01)

(58) Field of Classification Search
USPC .......................................................... 382/128
See application file for complete search history.

(56) References Cited

U.S. PATENT DOCUMENTS

| | | | |
|---|---|---|---|
| 9,589,374 B1* | 3/2017 | Gao | G06T 11/008 |
| 2010/0158332 A1 | 6/2010 | Rico et al. | |
| 2015/0230773 A1 | 8/2015 | Cho et al. | |
| 2016/0078614 A1 | 3/2016 | Ryu et al. | |
| 2016/0117818 A1 | 4/2016 | Park | |
| 2016/0188633 A1 | 6/2016 | Wang et al. | |
| 2017/0147905 A1 | 5/2017 | Huang et al. | |

FOREIGN PATENT DOCUMENTS

| | | |
|---|---|---|
| CN | 106339591 | 1/2017 |
| CN | 106372390 | 2/2017 |
| TW | 201232427 | 8/2012 |
| TW | I543750 | 8/2016 |
| TW | I552013 | 10/2016 |
| TW | 201724022 | 7/2017 |

OTHER PUBLICATIONS

Shan; Juan et al, "Computer-Aided Diagnosis for Breast Ultrasound Using Computerized Bi-Rads Features and Machine Learning Methods," Ultrasound in Medicine and Biology, vol. 42, No. 4, Dec. 2016, pp. 980-988.

Ceng; Jie-Zhi et al,"Computer-Aided Diagnosis with Deep Learning Architecture: Applications to Breast Lesions in US Images and Pulmonary Nodules in CT Scans," Scientific Reports, Apr. 15, 2016, pp. 1-13.

"Office Action of Taiwan Counterpart Application", dated Oct. 12, 2018, p. 1-p. 9.

* cited by examiner

FOCUS DETECTION APPARATUS AND METHOD THEREOF

CROSS-REFERENCE TO RELATED APPLICATION

This application claims the priority benefit of Taiwan application serial no. 106139059, filed on Nov. 10, 2017. The entirety of the above-mentioned patent application is hereby incorporated by reference herein and made a part of this specification.

BACKGROUND

Field of the Disclosure

The disclosure relates to a medical image detection, and in particular to a focus detection apparatus and a method thereof.

Description of Related Art

Computer Aided Detection (CADe) system has been widely used in clinical practice to automatically identify tumors, lesion or calcification point, to assist doctors in the diagnosis and treatment. However, there are still many shortcomings in today's computer-aided detection technology. For example, there is still accuracy problem such as risk of high false positive and the detection efficiency problem. Besides, it is often not possible to achieve accuracy and detection efficiency at the same time. For example, in order to improve detection accuracy, existing computer-aided detection may increase the overlap range of different Region of Interest (ROI) or Volume of Interest (VOI), which causes excessive amount of ROI or VOI and thus slowing down the detection speed. In view of the above, it is necessary to improve the focus detection technology for medical images.

SUMMARY OF THE DISCLOSURE

In view of the above, the disclosure provides a focus detection apparatus and a method thereof, which provide a more efficient sliding detection technology and effectively improve detection accuracy.

In the disclosure, a method for detecting a focus comprises the following steps: obtaining medical images; determining the size of the target focus and the sliding window, wherein the side length of the sliding window is at least twice the side length of the target focus; sliding the sliding window to scan the medical image, where a stride which the sliding window moves each time is not larger than the side length of the target focus; obtaining an area of interest based on the scan results; identifying the area of interest to determine the position of the focus.

In an embodiment of the disclosure, the step of identifying the area of interest to determine the position of the focus comprises the following steps: identifying the area of interests to determine the focus candidate; aggregating the focus candidates, among the focus candidates, of which the distance between each other is less than the dissimilarity threshold value into a group.

In an embodiment of the disclosure, the step of identifying the area of interest to determine the focus candidate comprises the following step: determining the focus candidate from the area of interest through machine learning technique.

In an embodiment of the disclosure, after the area of interest is identified to determine the position of the focus, the following steps are further included: adjusting the size of the target focus; scanning the medical image again according to the size of the adjusted target focus; determining the position of the focus according to the scan results of the target focuses with different sizes.

In the disclosure, a focus detection apparatus comprises a storage and a processor. The storage records several modules and medical images. The processor is coupled to the storage, and accesses and loads the modules recorded by the storage. The modules include an area of interest extraction module and a focus confirming module. The area of interest extraction module obtains the medical image, determines the size of the target focus and the sliding window, slides the sliding window to scan the medical image, and obtains the area of interest based on the scan result. The side length of the sliding window is at least twice the side length of the target focus, and the stride which the sliding window moves each time is not larger than the side length of the target focus. The focus confirming module identifies the identification range to determine the position of the focus.

In an embodiment of the disclosure, the sliding window has a side length that is twice the stride.

In an embodiment of the disclosure, the modules described above include a focus identifying module and a candidate aggregating module. The focus identifying module identifies the area of interest to determine the focus candidate. The candidate aggregating module aggregates the focus candidates, among the focus candidates, of which the distance between each other is smaller than the dissimilarity threshold value into a group.

In an embodiment of the disclosure, the focus identifying module determines a focus candidate from an area of interest through machine learning technique.

In an embodiment of the disclosure, the modules further include a multi-size aggregating module that adjusts the size of the target focus, the area of interest extraction module scans the medical image again according to the adjusted size of target focus, so that the focus confirming module determines the position of the focus based on the identification results of the target focuses with different sizes.

Based on the above, the size of the sliding window and the stride set by the embodiment of the disclosure are more efficient than conventional method where extracted area of interest is moved by one pixel only, and are further capable of improving detection accuracy by combining techniques such as machine learning, candidate aggregating, and multi-size aggregating.

In order to make the aforementioned features and advantages of the disclosure more comprehensible, embodiments accompanying figures are described in detail below.

DESCRIPTION OF EMBODIMENTS

Figure 1:
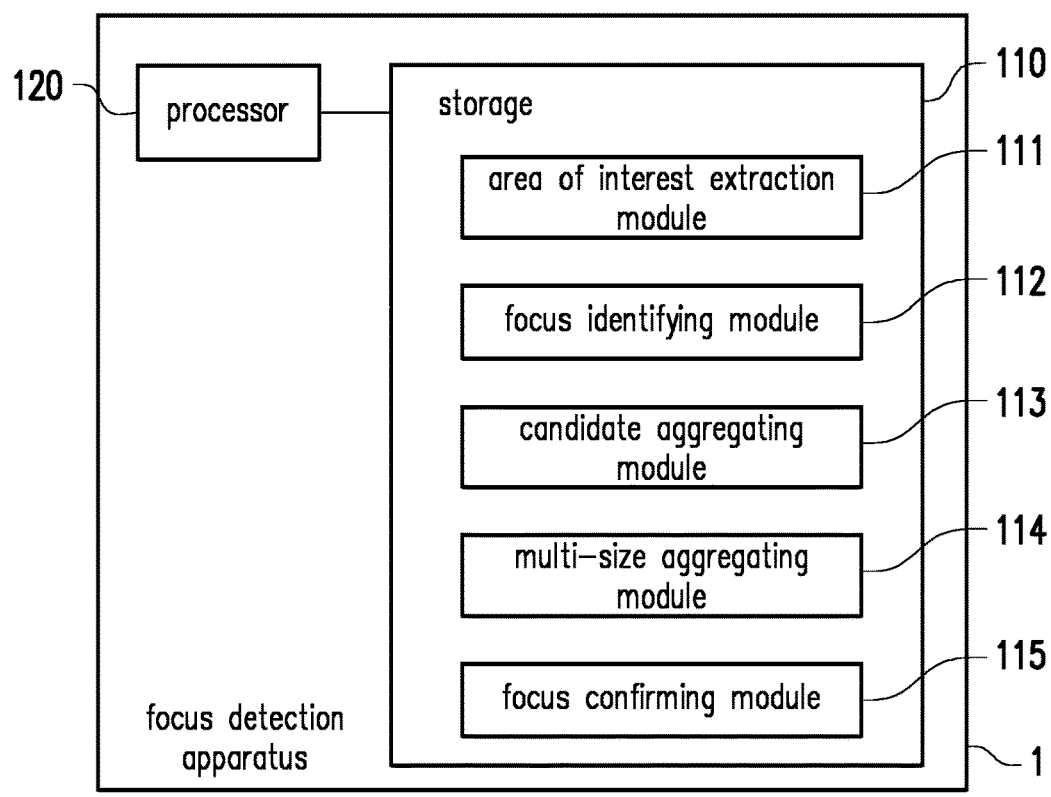
FIG. 1 is a block diagram of components of a focus detection apparatus according to an embodiment of the disclosure.

FIG. 1 is a block diagram of components of a focus detection apparatus 1 according to an embodiment of the disclosure. Referring to FIG. 1, the focus detection apparatus 1 at least includes but not limited to a storage 110 and the processor 120. The focus detection apparatus 1 may be a computer host, a server or even an instant medical image scanner.

The storage 110 may be any type of fixed or removable random access memory (RAM), read only memory (ROM), flash memory, conventional hard disk drive, solid-state drive or the like, and is used to record a software program such as an area of interest extraction module 111, a focus identifying module 112, a candidate aggregating module 113, a multi-size aggregating module 114, and a focus confirming module 115, various images such as dimensional or three-dimensional medical images (for example, automated breast ultrasound (ABUS), tomosynthesis, magnetic resonance imaging (MRI), etc., related data and information such as size of target focus, size of sliding window, stride, focus candidates, and position of focus. The foregoing modules, data, files and information are described in detail in the following embodiments.

The processor 120 is connected to the storage 110 and may be a central processing unit (CPU) or other programmable general purpose or specific purpose microprocessor, a digital signal processor (DSP), a programmable controller, an application specific integrated circuit (ASIC) or other similar components or a combination of the above. In the embodiment of the disclosure, the processor 120 is configured to perform all operations of the focus detection apparatus 1 and can access and execute the modules recorded in the storage 110.

Figure 2:
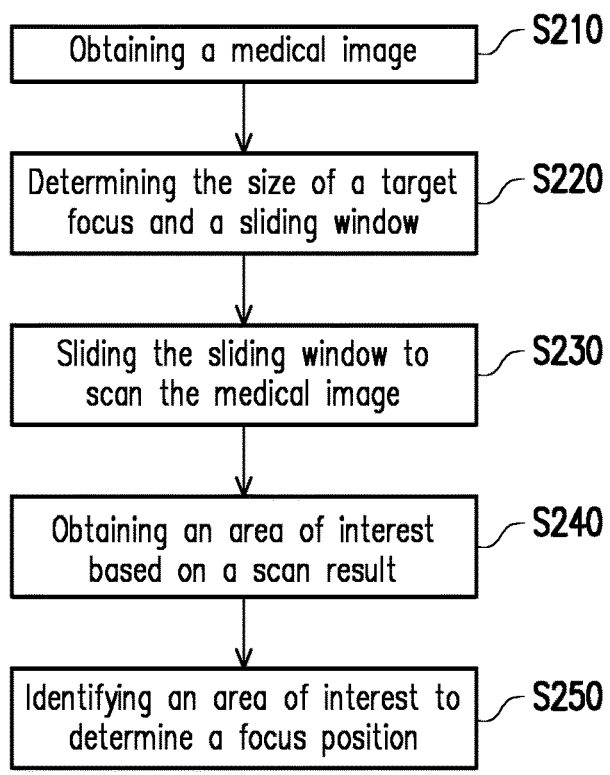
FIG. 2 is a flow chart of a focus detection method according to an embodiment of the disclosure.

In order to facilitate the understanding of the operation flow of the embodiment of the disclosure, the method for detecting the medical image by the focus detection apparatus 1 in the embodiment of the disclosure is described in detail below with reference to several embodiments. FIG. 2 is a flow chart of a focus detection method according to an embodiment of the disclosure. Referring to FIG. 2, the method of the embodiment is adapted to the focus detection apparatus 1 of FIG. 1. Hereinafter, the method in the embodiments of the disclosure is described with reference to various components and modules of the focus detection apparatus 1. The various processes of the method may be adjusted according to the actual implementation and are not limited thereto.

Medical images are created through capturing network packets, user upload, external or built-in storage media (e.g., flash drives, CDs, external hard drives, etc.) or even directly created by instant imaging through external or built-in image capturing units (e.g., cameras, video recorders, etc.) and stored in the storage 110, and the area of interest extraction module 111 may obtain one or more medical images (step S210).

Next, the area of interest extraction module 111 determines the size of the target focus and the sliding window (step S220). Specifically, in this embodiment, an object detection technology of the sliding window is used to extract a Region of Interest (ROI) for a two-dimensional image or a Volume of Interest (VOI) for a three-dimensional image. The area of interest extraction module 111 sets the size of various focuses such as a specific tumor, lesion, and microcalcification as the detection reference. Since the information (for example, shadow, intensity distribution, etc.) around the focus in the medical image helps to identify the focus, if the side length (assuming that side length may roughly include the side length of a square or a cube, the diameter of a circle or sphere, or the maximum vertical distance of other polygons or polyhedrons of target focus) of the target focus is LT, the side length of the sliding window is at least twice 2*LT (e.g., 2*LT, 2.5*LT, 2.6*LT, etc.) the side length of the target focus. When the sliding window (whose shape is square or cube, or other polygon or polyhedron) is slid each time, the image within the sliding window is scanned and the area of interest is extracted. In addition, the stride which the sliding window moves each time is also a major factor affecting the performance. Although the smaller stride is more likely to allow the focus in the medical image to be completely covered, eventually there will be an excessive number of area of interested that is extracted. In fact, the size of the focus should be no larger than the size of the target focus. As long as the sliding window is at least 2*LT and the stride is not greater than LT (e.g., LT, 0.8*LT, 0.5*LT, etc.), it can be ensured that the focus can be completely covered in at least one area of interest. Most preferably, if the stride is set as LT, the area of interest covering the whole focus may effectively reduce the execution time simultaneously. The side length of the sliding window may be set as twice the stride.

After the target focus, the sliding window, and the stride are determined, the area of interest extraction module 111 may slide the configured sliding window to scan the medical image (step S230). The area of interest extraction module 111 sequentially scan the medical image from a specific starting position while moving by the set stride, and scan the image in the sliding window each time when moving to a certain point, thereby obtaining one or more areas of interest based on the scan result (step S240).

Figure 3A:
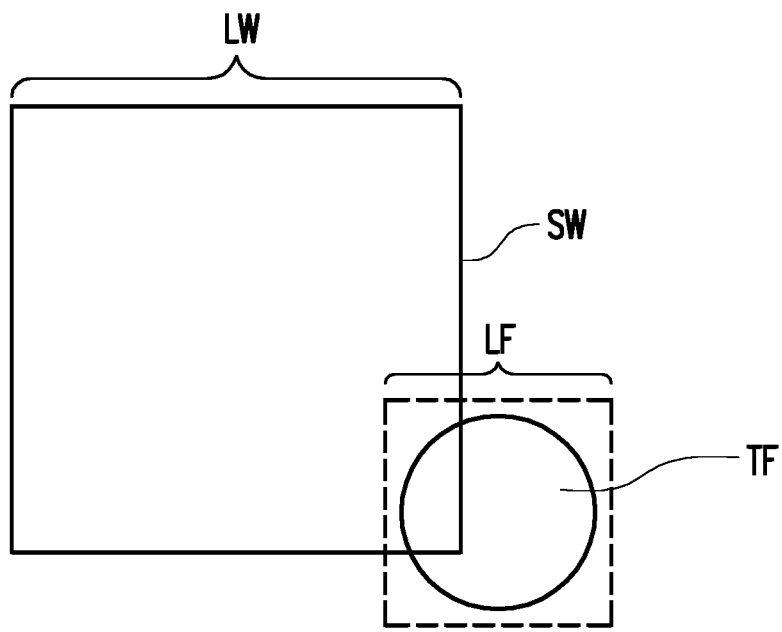
FIG. 3A-FIG. 3D are examples illustrating a sliding scan process.
Figure 3B:
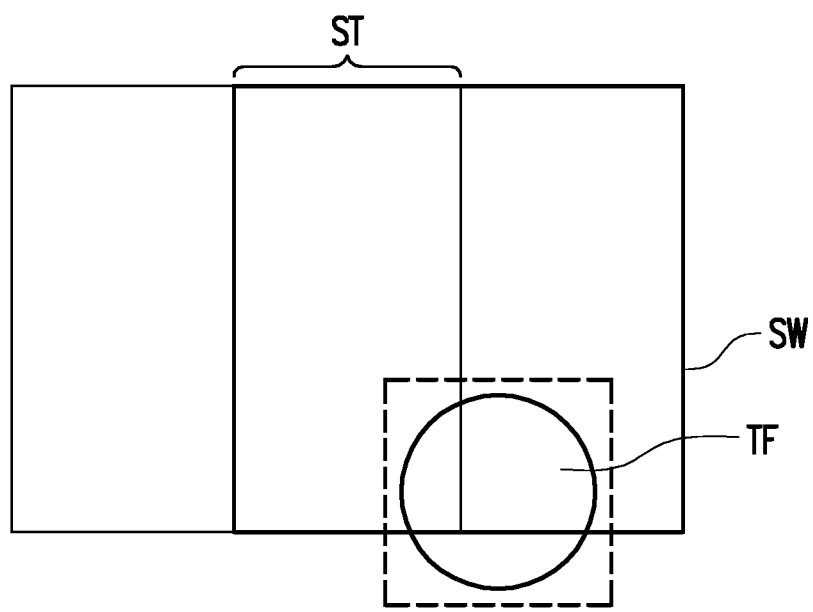
Figure 3C:
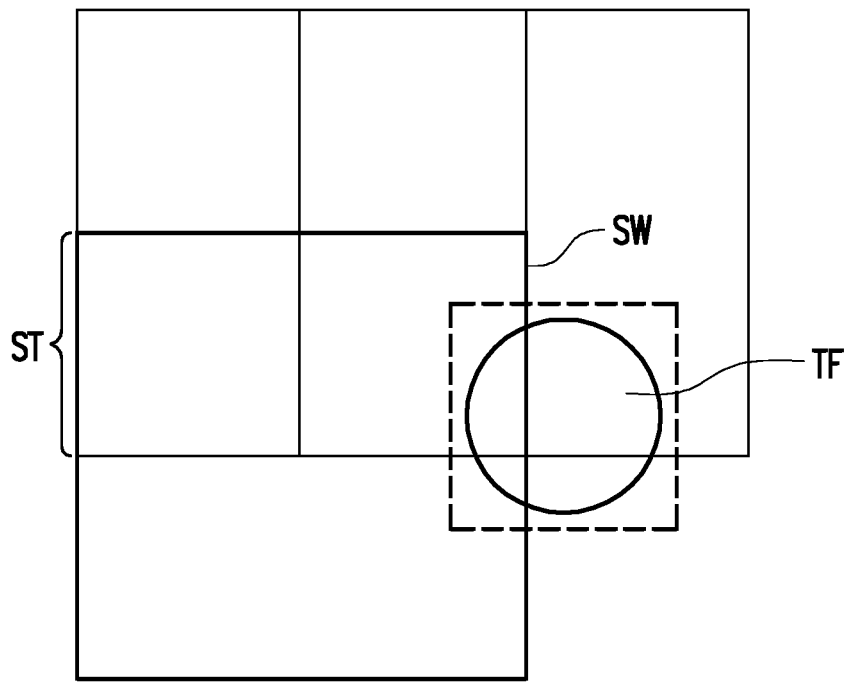
Figure 3D:
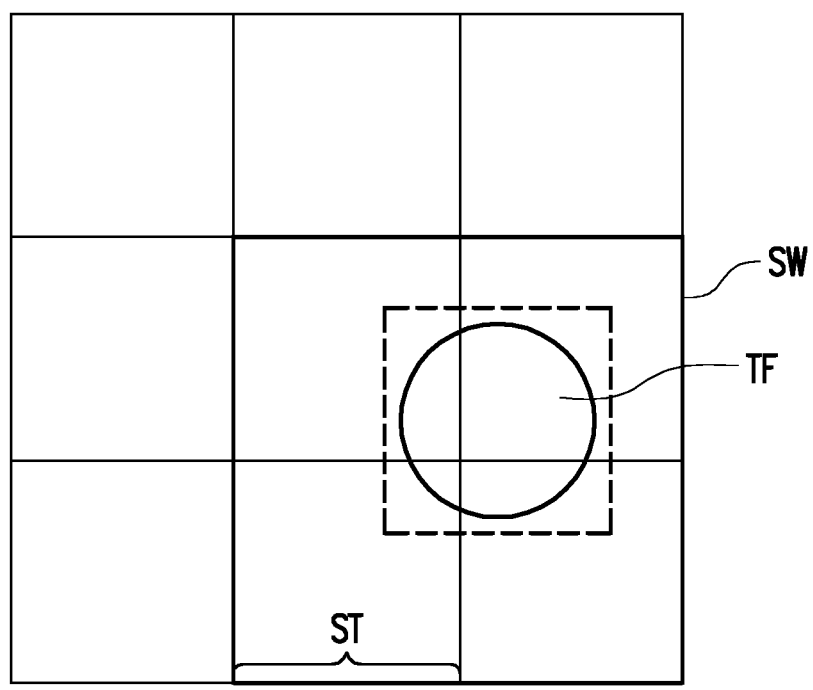

Taking FIG. 3A-FIG. 3D as an example, it is assumed that the medical image is a two-dimensional image, please refer to FIG. 3A first. If the side length of the target focus TF is LF, the side length LW of the sliding window SW (which has square shape) may be set as 2*LF, so that the sliding window SW may completely cover the target focus TF. Referring to FIG. 3B-FIG. 3D subsequently, the sliding window SW moves by the stride ST (set as LF, that is, half of side length LW of the sliding window SW) each time and obtains the ROI, and when the sliding window SW moves to the position shown in FIG. 3D, the whole focus can be completely covered.

After the area of interest is obtained, the area of interest may be further identified such that the focus identifying module 112 determines one or more focus positions (step S250). In particular, the focus identifying module 112 identifies these areas of interest to determine one or more focus candidates. In this embodiment, each of the area of interest determines the focus candidate through machine learning technique. The machine learning technique for image identification may be applied to the embodiment through various convolutional neural network (CNN) structures such as AlexNet, VGGNet-16, ResNet-34, other neural networks, and deep learning structures such as deep-brief network and recurrent neural network to estimate the likelihood of focuses that are present within the area of interest through the structures and then classified, and the area of interest with a likelihood greater than the threshold value serves as a focus candidate. It should be noted that, the deep learning technology is used in the embodiment of the disclosure due to its advantages in terms of accuracy and high execution efficiency. However, in other embodiments, other machine learning techniques such as decision tree, artificial neural network (ANN), support vector machine (SVM), and even other image detection techniques may be used to determine whether there is a focus within the area of interest.

It should be pointed out that the actual focus in the medical image may be covered by several overlapping focus candidates determined as described above (for example, the ROI in FIG. 3A-FIG. 3D detects the same focus and set as focus candidate). Accordingly, the candidate aggregating module 113 further aggregates the focus candidates, among the focus candidates, of which the distance between each other is less than the dissimilarity threshold value into a group, to determine the focus set. Specifically, the candidate aggregating module 113 is based on hierarchical clustering (HC). In the hierarchical cluster, the criteria for establishing linking lies in determining the degree of dissimilarity between the distances of the data set. When the degree of dissimilarity between two sets is less than the threshold value, the two sets may be combined into one cluster.

Figure 4:
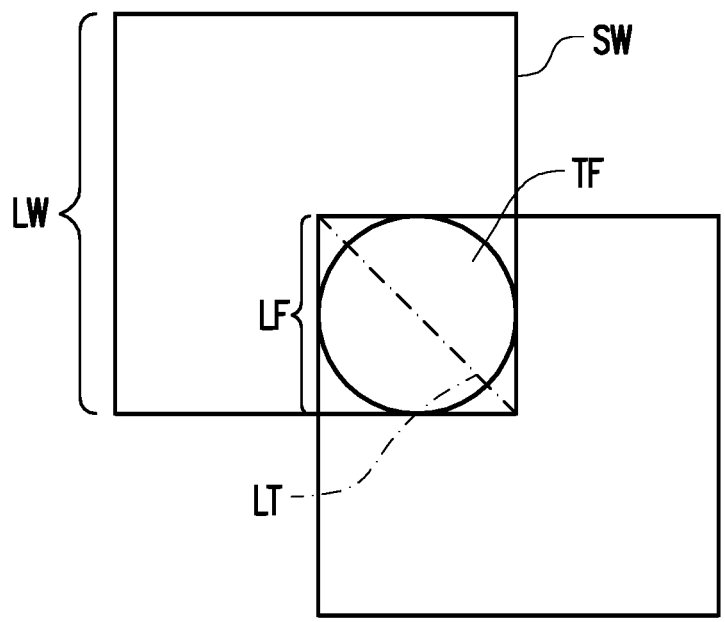
FIG. 4 is an example illustrating dissimilarity threshold value.

Please refer to the determination of the dissimilarity threshold value of FIG. 4. In the embodiment, since the longest Euclidean distance between the center point of two areas of interest that are able to cover the focus (the size is smaller than the side length LF of the target focus) is $\sqrt{3}LF$, the dissimilarity threshold value LT may be set as $\sqrt{3}LF$. The hierarchical clusters of this embodiment may be categorized into the following table (1) (assuming that a and b respectively represent the positions of the center points of two areas of interest):

TABLE 1

| Parameter | Numerical value |
|---|---|
| distance | Euclidean distance<br>$d(a, b) = \sqrt{\Sigma_i (a_i - b_i)^2}$,<br>i is the coordinate direction |
| Linking criteria | Single link (closest neighboring point)<br>$\min\{d(a, b): a \in A, b \in B\}$,<br>A, B represent different focus candidates |
| dissimilarity threshold | $\sqrt{3}LF$ |

Finally, all center points located in the same cluster are weight-averaged into a single position as the central point of the aggregating cluster, where the weight value assigned to each focus candidate is its estimated likelihood.

Figure 5A:
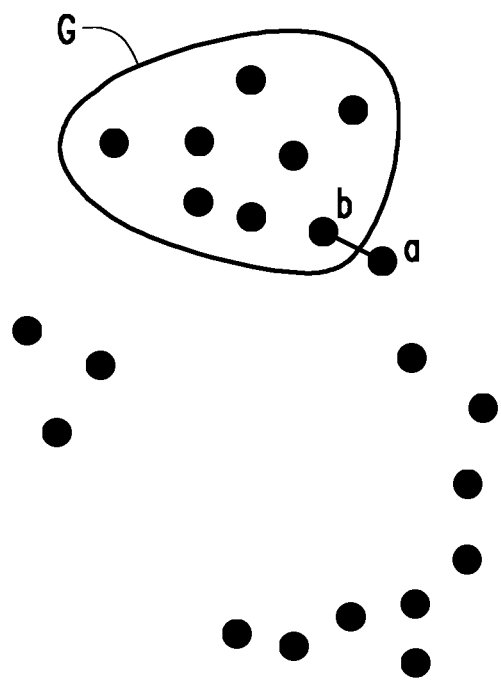
FIG. 5A-FIG. 5E are examples illustrating a candidate aggregating process.
Figure 5B:
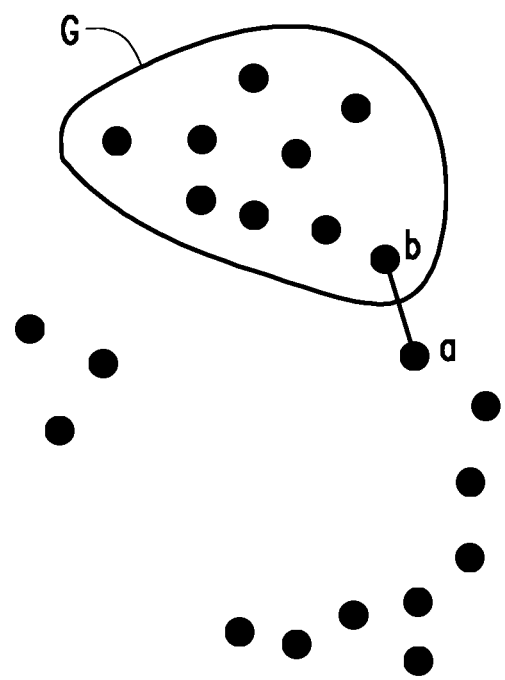
Figure 5C:
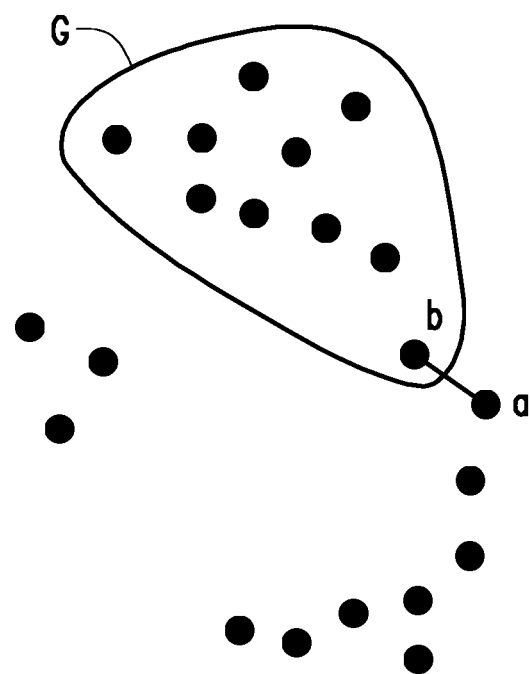
Figure 5D:
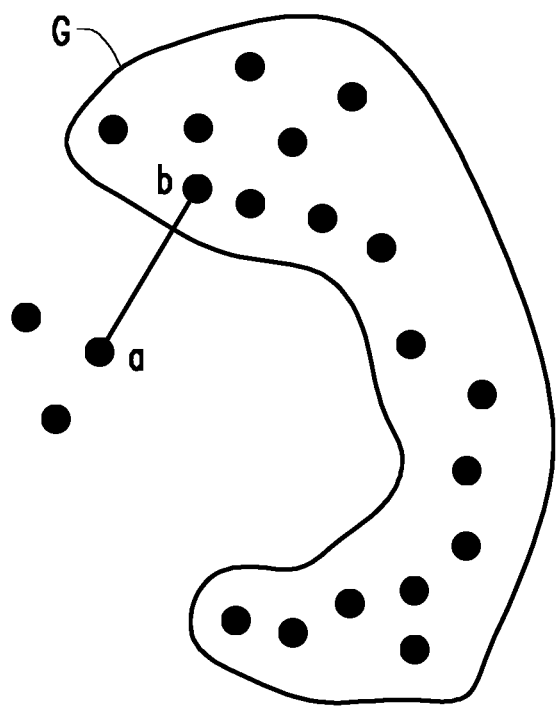
Figure 5E:
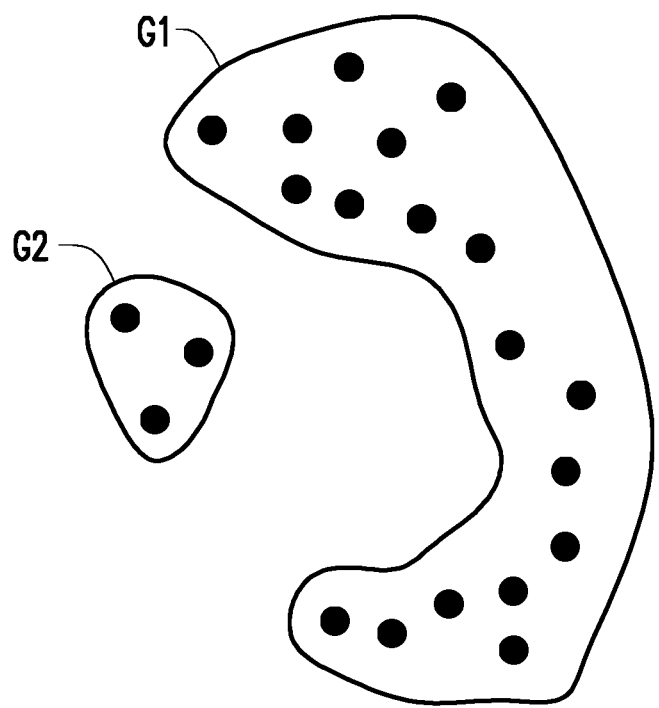

Take FIG. 5A-FIG. 5E as example, please refer to FIG. 5A-5C first, any focus candidate away from the nearest neighboring focus candidate at a distance less than the dissimilarity threshold is classified into the same group G. Further referring to FIG. 5D-FIG. 5E, the focus candidate away from the nearest neighboring focus candidate at a distance greater than the dissimilarity threshold is classified into different groups G1, G2. The focus candidates of the same group may be determined by the focus confirming module 115 as belonging to the same focus (hereinafter referred to as the focus set).

It should be pointed out that, when a lower dissimilarity threshold is used, more focus candidates are generated and they are closely distributed around the volume, and the rule of nearest neighboring is adopted by the final hierarchical cluster to classify excessive focus candidates into one group, causing difference in the range of actual focus covered by the focus set. Therefore, in order to reduce excessive aggregation, the group size (the number of focus candidates in a single group) has to be limited, and the focus candidates with higher likelihood should be aggregated first. In this embodiment, the maximum group size may be referred to as a degree of aggregating (DoA), and since the actual focus (the size of which should be smaller than the size (side length is LF) of the target focus) may be completely covered by eight areas of interest having a side length that is 2*LF, the optimal DoA is not greater than eight. It may be obtained that after classification by machine learning techniques, the focus candidate is chosen by deleting the area of interest having a focus likelihood less than the threshold value and the group size thereof is greater than DoA.

It should be noted that, the aforementioned dissimilarity threshold (i.e., $\sqrt{3}LF$) and DoA (i.e., 8) are derived from the three-dimensional volume of interest (VOI), but the value might change due to the dimensions (e.g., two-dimensional, three-dimensional) of the medical image or area of interest, the disclosure provides no limitation in this regard.

In fact, the position of the focus may be confirmed through the foregoing steps, but in order to further improve the accuracy of detection, a multi-size aggregating module 114 adjusts the size of the target focus to be detected, and the area of interest extraction module 111 scans the medical image again according to the adjusted size of the target focus to obtain an area of interests of different sizes. The multi-size aggregating module 114, according to the identification results of the target focuses with different sizes, makes the focus confirming module 115 to confirm the focus position through maximum likelihood or weighted average maximum likelihood. In other words, the foregoing steps are performed multiple times (two times, three times, five times, etc.) with target focuses of different sizes, and the focus sets determined by the target focuses with different sizes may overlap each other eventually. Since the focus sets determined by the target focuses with different sizes are formed by aggregating several focus candidates, the maximum likelihood of the focus candidates may be used to represent the likelihood of each of the focus sets. Thereafter, the multi-size aggregating module 114 may select the focus set with the highest likelihood and discard the other sets covering the center of the focus set until there is no other overlapping set, and the focus confirming module 115 may confirm the position and size of the focus based on the final focus set.

In summary, in the object detection technology of the sliding window provided in the embodiment of the disclosure, optimal parameters (i.e., the side length of the sliding window is at least twice the side length of the target focus, and each stride is not larger than the side length of the target focus) are adopted for medical images of different dimensions (for example, two-dimensional, three-dimensional) to obtain the region of interest or volume of interest, thereby increasing the computational time while maintaining accuracy. Then, machine learning techniques, candidate aggregation and multi-size aggregating steps are combined to further assist in confirming the position and size of focus, bringing breakthrough in computer-aided detection technology.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A focus detection method, comprising:
   obtaining a medical image;

determining a size of a target focus and a sliding window, wherein a side length of the sliding window is at least twice a side length of the target focus;

sliding the sliding window to scan the medical image, wherein a stride which the sliding window moves each time is not greater than a side length of the target focus;

obtaining at least one area of interest based on a scan result; and identifying the at least one area of interest to determine at least one focus position.

2. The focus detection method according to claim 1, wherein the side length of the sliding window is twice the stride.

3. The focus detection method according to claim 1, wherein the step of identifying the at least one area of interest to determine the at least one focus position comprises:

identifying the at least one area of interest to determine at least one focus candidate; and aggregating focus candidates of the at least one focus candidate having a distance between each other less than a dissimilarity threshold value into a group.

4. The focus detection method according to claim 3, wherein the step of identifying the at least one area of interest to determine the at least one focus candidate comprises:

determining the at least one focus candidate from the at least one area of interest through a machine learning technique.

5. The focus detection method according to claim 1, wherein after identifying the at least one area of interest to determine the at least one focus position, further comprising:

adjusting the size of the target focus;

scanning the medical image again according to an adjusted size of the target focus; and determining the at least one focus position according to scan results of target focuses with different sizes.

6. A focus detection apparatus, comprising:

a storage, recording a plurality of modules and a medical image; and a processor, coupled to the storage, and accessing and loading the modules recorded by the storage, the modules comprising:

an area of interest extraction module, obtaining the medical image, determining a size of a target focus and a sliding window, sliding the sliding window to scan the medical image, and obtaining at least one area of interest according to a scan result, wherein a side length of the sliding window is at least twice a side length of the target focus, and a stride which the sliding window moves each time is not greater than the side length of the target focus; and a focus confirming module, identifying the at least one area of interest to determine at least one focus position.

7. The focus detection apparatus according to claim 6, wherein the side length of the sliding window is twice the stride.

8. The focus detection apparatus according to claim 6, wherein the modules further comprise:

a focus identifying module, identifying the at least one area of interest to determine at least one focus candidate; and a candidate aggregating module, aggregating focus candidates of the at least one focus candidate having a distance between each other less than a dissimilarity threshold value into a group.

9. The focus detection apparatus according to claim 8, wherein the focus identifying module determines the at least one focus candidate from the at least one area of interest through a machine learning technique.

10. The focus detection apparatus according to claim 6, wherein the modules further comprise:

a multi-size aggregating module, adjusting the size of the target focus, and the area of interest extraction module scanning the medical image again according to an adjusted size of the target focus, so that the focus confirming module determines the at least one focus position according to identification results of target focuses with different sizes.

\* \* \* \* \*